Figure 3:
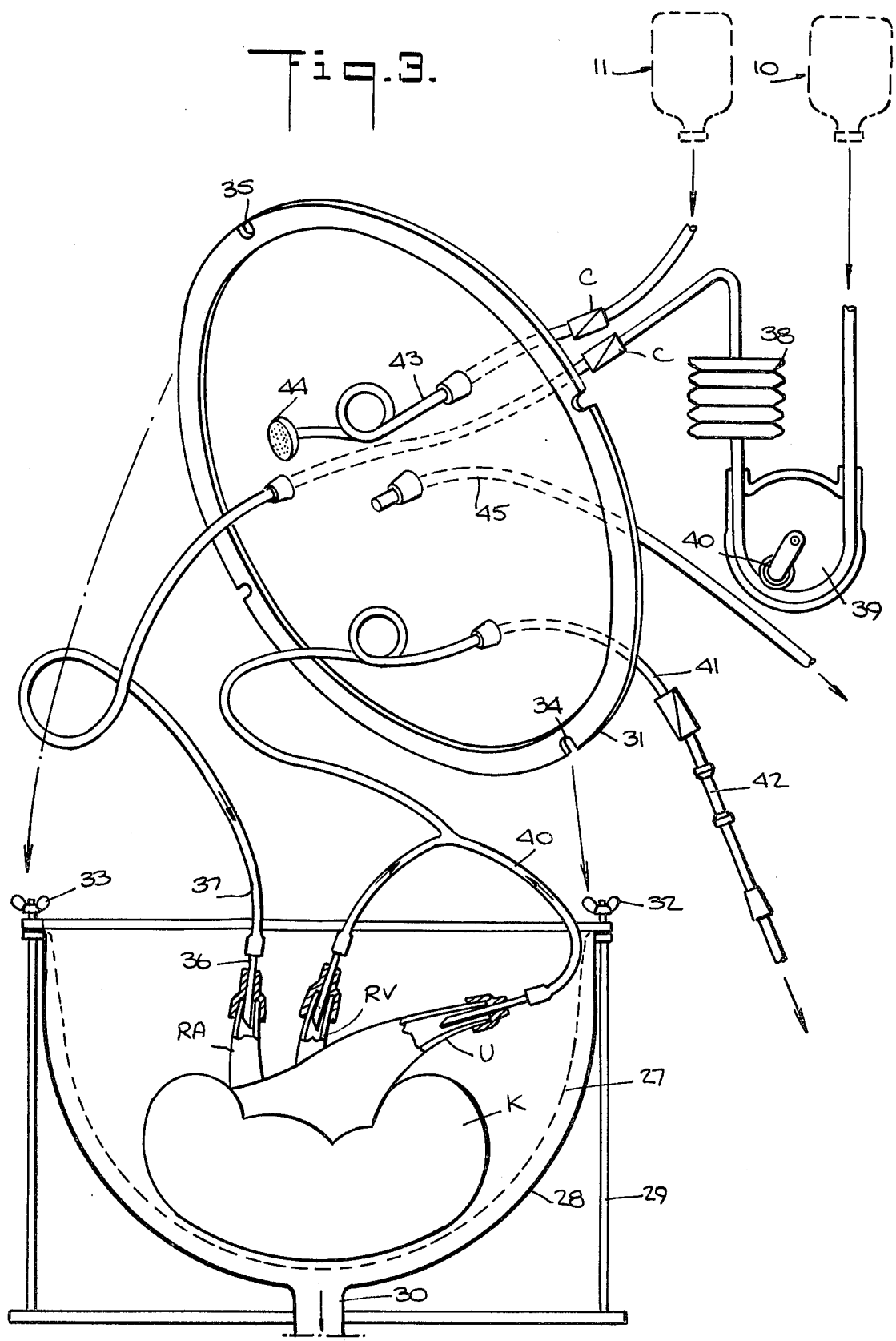

United States Patent [19]

Guibert

[11] Patent Number: 4,473,637
[45] Date of Patent: Sep. 25, 1984

[54] SYSTEM FOR PROCESSING AN ORGAN PREPARATORY TO TRANSPLANT

[75] Inventor: Raul Guibert, Los Angeles, Calif.

[73] Assignee: Guibert, Colman & Associates, Los Angeles, Calif.

[21] Appl. No.: 440,606

[22] Filed: Nov. 10, 1982

[51] Int. Cl.³ .......................... A01N 1/02; C12M 1/00
[52] U.S. Cl. .......................................... 435/1; 435/287
[58] Field of Search ............................ 435/1, 284, 287

[56] References Cited

U.S. PATENT DOCUMENTS

| | | | |
|---|---|---|---|
| 3,406,531 | 10/1968 | Swenson et al. | 435/1 X |
| 3,607,646 | 9/1971 | Roissart | 435/1 |
| 3,632,473 | 1/1972 | Belzer et al. | 435/1 |
| 3,777,507 | 12/1973 | Burton et al. | 435/1 X |
| 3,810,367 | 5/1974 | Peterson | 435/1 X |
| 3,881,990 | 5/1975 | Burton et al. | 435/1 |
| 3,892,628 | 7/1975 | Thorne et al. | 435/1 |
| 3,914,954 | 10/1975 | Doerig | 435/1 X |
| 4,186,565 | 2/1980 | Toledo-Pereyra | 435/1 X |

OTHER PUBLICATIONS

J. L. Alexander, M.D. et al., Surgery, vol. 67, No. 6, pp. 944–950; 1970.
J. A. Long, J. Lab. and Clinical Medicine, vol. 32, pp. 300–310; 1947.

Primary Examiner—Robert J. Warden
Attorney, Agent, or Firm—Michael Ebert

[57] ABSTRACT

A system for processing an organ such as a kidney so as to render it suitable for storage, shipment and eventual transplantation. After its removal from a donor, the organ is cradled in a net suspended within a basin. A preservative fluid initially at normal blood temperatures progressively cooled to avoid thermal shock, the fluid being pumped through the organ to flush out its natural fluids. The pumping action is such as to simulate that of the heart and its associated circulatory system. The exterior of the organ is chilled by simultaneously introducing the preservative fluid into the basin. After this chilling procedure is completed, the cradle carrying the cooled organ is transferred to a basin disposed in a thermally-insulated shipping box which is then filled with chilled preservative fluid and maintained at a desired low temperature level by an associated refrigeration unit. Just prior to transplantation, the cradle carrying the organ is removed from the box and the organ is again flushed, using the same procedure as in chilling but in reverse, the preservative fluid being raised to a temperature level close to normal blood temperature. Upon completion of this procedure, the organ is in condition for transplantation.

7 Claims, 4 Drawing Figures

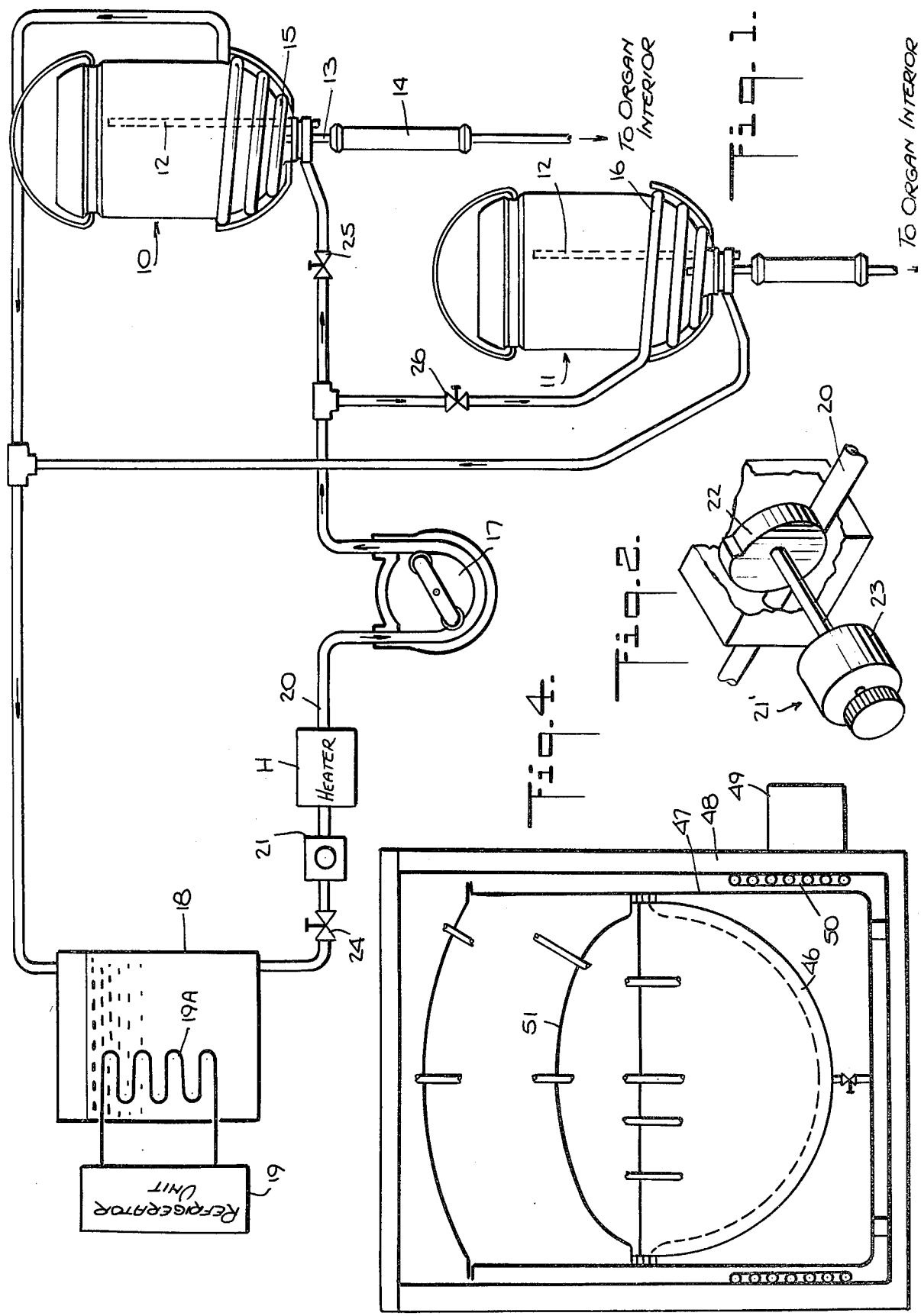

SYSTEM FOR PROCESSING AN ORGAN PREPARATORY TO TRANSPLANT

BACKGROUND OF INVENTION

This invention relates generally to techniques for processing an organ removed from a donor so as to render it suitable for storage, shipment and eventual transplantation, and more particularly to a system which facilitates a chilling procedure for an organ after it is removed from a donor so that the organ may be maintained in a healthy condition for a relatively prolonged period and shipped in this condition to a transplantation site where a heating procedure is carried out just prior to transplantation.

While the invention shall be described in connection with the processing of kidneys, it is to be understood that similar chilling and heating procedures using essentially the same technique are applicable to other organs such as the liver and the pancreas.

The kidneys are two reddish, bean-shaped organs near the vertebral column at the small of the back, the left kidney lying somewhat higher than the right. The purpose of the kidney is to separate urea and other waste products from the blood. For life to be maintained, at least one kidney must function properly. Blood entering the kidney through the renal artery is returned to circulation in purified form through the renal vein. The waste in the form of urine is excreted by way of the urethra and the bladder.

A kidney is composed of a large number of functional units called nephrons with their associated ducts and blood vessels. A nephron has two parts; namely, the corpuscle which is a bundle of capillaries (glomerulus) enclosed in a capsule, and a tubule which is a long, thin tube leading from the capsule to a collecting tube. Blood flows through the incoming arteriole to the glomerulus, the blood pressure forcing everything in the blood except cells and proteins to filter through the thin walls of the capillaries into the capsule. The remaining blood then flows through the outgoing arteriole to capillaries surrounding the tubule. The resultant filtrate forms at a rate depending on blood pressure and the highly variable rate of blood flow through the glomerulus. The filtrate passes from the capsule into the tubule.

Kidneys are subject to congenital malfunction, physical injury, infections such as Bright's disease, stone formation, arteriosclerosis and tumors. It is for this reason that artificial kidneys are now standard equipment in hospitals where they serve to cleanse and otherwise alter the patient's blood flushed through it. Where a kidney is irreparably affected, it may be replaced surgically by transplantation.

The concern of the present invention is with the processing of a healthy kidney after it has been extracted from a donor and before it is transplanted in a recipient, the kidney during this period being "in limbo".

The present "in limbo" practice, after the kidney is surgically removed from the donor is to flush the organ with a kidney preservative liquid, such as the electrolyte solution 5A7810 marketed by Travenol Laboratories, Inc. of Deerfield, Ill. This solution contains a high concentration of potassium and phosphate and is compatible with blood. The solution, before infusion in the kidney, is chilled in ice to 0°–4° C. (32°–39.2° F.).

The chilled solution is dispensed from a solution bottle held at a height sufficient to produce a continuous gravity flow, the kidney being flushed until the cortex is pale and the effluent is clear, evidencing the disappearance of blood from the kidney. This action is carried out with the kidney in a sterile storage container. After the preservative solution has been perfused, the remainder of the solution is dispensed into the storage container which is then sealed. The storage container housing the flushed organ is then placed within a thermally-insulated shipping carton in which it is surrounded with ice. The ice does not come into direct contact with the organ in the storage container.

A kidney, "in limbo" is subject to rapid biological decay unless steps are taken to maintain it in a healthy state for the period elapsing between its time of removal from the donor and the time of transplantation. With existing techniques, the "in limbo" period must be relatively short and is numbered in hours rather than days. Hence it is not presently possible to transport a kidney extracted from a donor in California to a recipient, say, in London; for the time involved is beyond that which can be tolerated with existing procedures.

And even if transplantation could be arranged to take place within a few hours after the kidney is extracted, conventional preservation and storage techniques do not ensure a healthy organ; hence a significant percentage of transplants involve kidneys which do not function properly in the recipient, possibly because of damage to the kidney during the "in limbo" period. In this regard, reference is make to the article by Lee et al., "Medical Complications of Renal Transplantations" in the *Supplement to Urology*, June 1977, Vol. IX, No. 6.

To preserve a kidney, it should be maintained in a cold state so that the metabolic needs of the kidney are kept at a minimum. However, one cannot freeze a kidney; for the resultant ice crystals would destroy its cellular structure. Hence to effect preservation, it is essential that the kidney be brought as rapidly as possible to a temperature close to its freezing point without, however, subjecting it to thermal shock, and that the kidney be thereafter maintained at this low temperature until just prior to transplantation, when its temperature must be returned to a level close to body temperature.

In the prior technique, the preservation solution in the gravity-flow infusion bottle is at a temperature of 0° to 4° C., which means that the kidney processed thereby, because of poor heat transfer, will, after flushing, be cooled to a temperature somewhat above 4° C. or 39.2° F. While the flushed kidney in the sterile storage container is thereafter subjected to cooling by ice in the transportation carton, it must be borne in mind that an organ has poor thermal conductivity, and that it takes a significant amount of time for the kidney in the storage container to be adequately chilled by the exterior ice. This time factor may be damaging to the kidney.

Moreover, the flushing procedure which involves continuous gravity flow through the complex network of kidney vessels may not result in effective penetration, for this flow is not analogous to that encountered in vivo. In the human circulatory system, blood is caused to flow as a consequence of the force exerted by the periodic contraction of the heart, which undergoes a regular cyclic contraction (systole) followed by relaxation (diastole). The amount of blood pressure depends on the cardiac output; that is, the volume of blood pumped out of the heart per minute and arterial resistance. The blood vessel network in the kidney is adapted to operate in conjunction with the heart pump; and when preservation fluid is perfused therethrough continuously under gravity pressure rather than under pulsatory pressure in a manner simulating the action of the circulatory system, adequate penetration of the fluid in the kidney may not be realized.

Moreover, in existing techniques the kidney is not stored in its sterile container in a manner isolating it from mechanical shocks, and it may be damaged in handling and transport.

SUMMARY OF INVENTION

In view of the foregoing, the main object of this invention is to provide an improved technique and a system based thereon for processing an organ removed from a donor so as to render it suitable for storage, transportation, and eventual transplantation into a recipient.

More particularly, an object of this invention is to provide a system which facilitates a chilling procedure for an organ after it is removed from a donor so that the organ may be maintained in a healthy condition for a relatively prolonged period and shipped in this condition to a transplantation site at which a similar heating procedure is carried out just prior to transplantation.

Also an object of this invention is to provide apparatus to facilitate a chilling and heating procedure for an organ, which apparatus acts to pump a preservative fluid through the organ in a manner simulating the action of the heart and its associated circulatory system whereby the fluid fully penetrates the vascular system of the organ.

Yet another object of this invention is to provide apparatus of the above type in which the preservative fluid pumped into the organ is progressively chilled or heated to avoid thermal shock to the organ.

Briefly stated, these objects are attained in a system for processing an organ such as kidney so as to render it suitable for storage, shipment and eventual transplantation. After its removal from a donor, the organ is cradled in an elastic net suspended within a basin. A preservative fluid initially at normal blood temperature is progressively cooled to avoid thermal shock, the fluid being pumped through the organ to flush out its natural fluids. The pumping action is such as to simulate that of the heart and its associated circulatory system. The exterior of the organ is chilled by simultaneously introducing progressively-cooled preservative fluid into the basin.

After this chilling procedure is completed, the cradle carrying the cooled organ is transferred to a basin disposed in a thermally-insulated shipping box which is then filled with chilled preservative fluid and maintained at the desired low temperature level by an associated refrigeration unit. Just prior to transplantation, the cradle carrying the organ is removed from the box and the organ is again flushed, using the same procedure as in chilling but in reverse, the preservative fluid being progressively raised to a temperature level close to normal body temperature. Upon completion of the procedure, the organ is in condition for transplantation.

OUTLINE OF THE DRAWINGS

For a better understanding of the invention as well as other objects and further features thereof, reference is made to the following detailed description to be read in conjunction with the accompanying drawings, wherein:

FIG. 1 schematically illustrates the apparatus included in a system in accordance with the invention for progressively cooling or heating preservation fluid to be used to process an organ;

FIG. 2 is a perspective view of the cam assembly for effecting a progressive heating or cooling action;

FIG. 3 schematically illustrates the apparatus for pumping the preservative fluid through the organ being processed; and FIG. 4 illustrates, in section, a shipping box for the organ.

DESCRIPTION OF THE INVENTION

The Preservative Liquid Cooling Apparatus

Referring now to FIG. 1, there is shown apparatus employed in a system in accordance with the invention for progressively chilling preservative fluid contained in bottles, pouches or containers 10 and 11. The chilled fluid in bottle 10 is used to flush the vascular system of a kidney, and the chilled fluid in bottle 11 to simultaneously chill the exterior of this organ.

Bottle 10 is provided with an air vent tube 12 extending above the fluid therein and an outlet tube 13 which conducts the fluid through a transparent observation or drip tube 14 to the interior of the organ. Surrounding the lower portion of bottle 10 is a heat exchange coil 15 which acts to draw heat from the preservation fluid. Bottle 11 is similar to bottle 10 and is provided with a heat exchange coil 16 for the same purpose.

Flowing through both heat exchange coils 15 and 16 is a liquid thermal agent such as an anti-freeze solution drawn by a peristaltic pump 17 from a supply tank 18, the agent therein being cooled by a heat exchange coil 19A coupled to a temperature control unit 19.

Any conventional form of regulated refrigerator unit may be used to maintain the liquid agent at a substantially constant temperature close to zero degrees centigrade.

Tank 18 is coupled to pump 17 through a flexible line 20 associated with a cam assembly 21 which serves to modulate the flow of refrigerant going into the pump. As shown separately in FIG. 2, cam assembly 21 is constituted by a shaped cam 22 which engages flexible line 20 and is driven by an adjustable timer and gear motor 23. In the course of a full revolution which takes place in a pre-set timing interval that runs the full length of the operating cycle of the apparatus, cam 22 exerts a progressively decreasing pressure on line 20, thereby progressively increasing the flow of refrigerant through the line. Line 20 goes through a heating unit H which when operative acts to heat the agent running through the line at a temperature equivalent to normal blood temperature.

At the start of the timing cycle, no refrigerant flows into pump 17 and no refrigerant is pumped thereby into cooling coils 15 and 16 for bottles 10 and 11, for in the initial period, heater H is activated and cam 20 is deactivated so that the liquid agent assumes the blood temperature. Then the heater is deactivated and the cam activated so that the volume of agent fed into pump 17 gradually rises to increase the flow thereof into the coils. As a consequence, preservative fluid flowing out of bottles 10 and 11 is at blood temperature and undergoes no cooling; but as flow from the bottles continues, the fluid is progressively cooled until a point is reached where the fluid temperature is close to the freezing point.

This progressive chilling action which in the course of a timing cycle goes from blood temperature to a point close to freezing is essential to avoid subjecting the kidney being treated by the preservative fluid from experience an abrupt thermal shock which may be damaging to its condition. Valve 24 interposed between tank 17 and cam assembly 21 makes it possible to set the flow rate into the assembly or to cut off flow. Valve 25 in the input line to coil 15 for bottle 10 makes it possible to control flow into this coil, valve 26 in the input to coil 16 for bottle 11 serving the same function.

The reason separate bottles 10 and 11 each containing the same preservative fluid are provided rather than a common bottle, is that bottle 10 constitutes a supply whose fluid is pumped into the interior of the organ in a manner simulating the action of the heart, whereas bottle 11 constitutes a supply whose fluid is fed continuously to the exterior of the organ.

The Kidney Cooling Apparatus

Referring now to FIG. 3, there is shown a kidney K that has surgically been removed from a donor, the kidney including a renal artery RA, a renal vein RV and a urethra U. The separated kidney is cradled by a net 27 of sterile synthetic plastic filamentary material. This net is suspended within a basin 28, preferably of stainless steel, whose rim is supported by a frame 29, the basin having a drain 30. The dimensions of the net relative to the basin are such as to define a space therebetween so that no portion of the kidney makes contact with the metal basin and the kidney is isolated from mechanical shock forces. The net is preferably elastic.

The basin is closed by a removable cover 31 which is secured thereto by wing nuts 32 and 33 received on screws mounted on the frame, these screws going through diametrically-opposed notches 34 and 35 in the cover.

Coupled to the renal artery RA by means of a suitable catheter 36 is a flexible line 37 which extends through cover 31 and terminates in an expansible bellows 38. Bellows 38 is supplied with chilled preservative fluid drawn from bottle 10 by means of a peristaltic pump 39 having a single rotating roller arm 40 so tht in the course of each full cycle of rotation, fluid is pumped into bellows 38 during a half cycle thereof. Thus pump 39 periodically feeds pulses of preservative fluid into bellows 38, each pulse acting to fill and expand the bellows. In the interval between successive pulses, the bellows contract to discharge the preservative fluid into line 37 leading into the renal artery RA.

The pulse rate of pump 39 and the pulse wave created by the bellows are such as to simulate the action of the circulatory system in which the heart pumps blood into the arteries, each pulse of blood acting to dilate the arteries which then proceed to contract to force the blood into the system. Thus preservative fluid is pumped into the vascular system of the separated kidney in essentially the same manner as blood is pumped therein when the kidney is in place. This heart-like action serves to cause the fluid to penetrate all blood vessels in the kidney and to flush out the blood therefrom.

Renal vein RV and urethra U are coupled by a forked line 40 extending through the cover 31 and leading to a discharge line 41 which includes an observation tube 42 so that the color of the discharge may be observed to determine whether flushing has been effected.

Though the preservative fluid is chilled to a temperature somewhat below the temperature at which the kidney is to be held (i.e., 3° C.) because it flows therethrough in a pulsatory manner, the no-flow intervals between pulses permits heat transfer to take place from the blood vessels to the internal structure of the kidney, thereby preventing excessive chilling of the vessel region. In this manner, the entire body of the kidney is uniformly reduced in temperature to the desired low level in a relatively short period.

The exterior of the kidney is chilled by simultaneously introducing the cooled perservative fluid from bottle 11 by way of a line 43 extending through the cover and terminating in one or more spray heads 44. The preservative fluid sprayed into the basin 28 fills the space between net 27 and the basin and makes contact with the entire outer surface of the kidney.

Air displaced in the basin by the preservative fluid is exhausted to the atmosphere through a line 45 extending through the cover. The lines passing through the cover are provided with disconnectable couplers, such as coupler C. Thus the apparatus shown in FIG. 3 acts to carry out the chilling procedure.

Storage and Transplantation

After the chilling procedure is completed, the net cradling the kidney and the cover are removed from basin 28 and transferred to a basin 46 mounted within a tank 47 placed within a thermally-insulated shipping box 48. This box is associated with a refrigeration unit 49 whose heat exchange coils 50 are mounted within the box. (See FIG. 4)

Basin 46 is filled with preservative fluid, and the region between cover 31 and protective cap 51 is also filled with preservative fluid as well as the tank itself, the fluid filled tank 47 being held at a suitable low temperature by the regulated refrigeration unit. In this way the kidney may be held in storage and shipped to a tranplantation site.

When the kidney held in the storage is to be transplanted, the cradled kidney is removed from the box and transferred to a basin of the type in FIG. 3 supported in a frame. Thus the apparatus provided at transplantation site is effectively a duplicate of that at the chilling site, except that means are provided to heat not to chill the preservative fluid. Then the kidney is again flushed with preservative fluid, using the reverse procedure as in chilling, but this time the fluid is heated progressively to a temperature level approaching normal blood temperature, so that the kidney transplanted into the recipient is compatible with the temperature of the circulatory system of the recipient.

In summary, therefore, a system in accordance with the invention makes use of apparatus to facilitate a chilling procedure, apparatus to facilitate a storage and shipment procedure and apparatus to facilitate a heating procedure, the kidney in all procedures being held in a net suspended within a basin.

Thus while the level of skill in modern surgery is such that a kidney can be removed from a donor and used to replace a defective kidney in a recipient, the surgeon's skill is of no avail if the transplanted kidney has been impaired while "in limbo". A system in accordance with the invention serves to prolong the acceptable "in limbo" period so that even if several days are required before the removed kidney is available to the recipient, the kidney will remain healthy and thereby improve the chances for a successful transplantation.

While there has been shown and described a preferred embodiment of A System for Processing an Organ Preparatory to Transplant in accordance with the invention, it will be appreciated that many changes and modifications may be made therein without, however, departing from the essential spirit thereof.

I claim:

1. Apparatus for maintaining an organ removed from the body of a donor in a healthy state for subsequent transplantation, said apparatus comprising means to flush the removed organ by pumping a preservative fluid through the vascular system thereof in a pulsatory stream for a predetermined period in a manner simulating the activity of the heart and its associated circulatory system, and means including a heater and a refrigerator operative during said period to progressively reduce the temperature of said preservative fluid from an initial level close to that of normal blood temperature to a temperature approaching the freezing point to avoid subjecting the organ to an abrupt thermal shock damaging to its condition.

2. Apparatus as set forth in claim 1, wherein said means to flush the organ includes a pump producing periodic pulses of the preservative fluid which are supplied to an expansible bellows caused by each pulse to expand, the bellows collapsing in the interval between pulses.

3. Apparatus as set forth in claim 1, further including:
   A. means to concurrently subject the exterior of the organ to said preservative fluid; and
   B. means to progressively reduce the temperature of the preservative fluid to which the exterior of the organ is exposed to cause the organ to assume a substantially uniform low-temperature above its freezing point.

4. Apparatus as set forth in claim 3, wherein said means to reduce the temperature of the preservative fluid is constituted by a timed motor-driven rotary cam which engages a flexible line conducting a liquid agent for chilling the fluid, said cam in the course of a full revolution progressively increasing the flow of the refrigerant in the course of the period.

5. Apparatus as set forth in claim 4, wherein said fluid is contained in a bottle surrounded by a heat exchange coil through which said refrigerant from said line is caused to flow.

6. Apparatus as set forth in claim 3 wherein said organ being treated is held in a net suspended within a basin.

7. Apparatus as set forth in claim 6, wherein said organ is a kidney and means to admit said preservative fluid into the renal artery of the kidney and means to discharge the fluid from the renal vein and urethra.

* * * * *